United States Patent
Davies et al.

(10) Patent No.: US 7,211,243 B2
(45) Date of Patent: May 1, 2007

(54) TERMINAL AMINOFUNCTIONAL POLYSILOXANE HAIR CONDITIONING COMPOSITIONS AND THEIR USE IN HAIR COLORING COMPOSITIONS

(75) Inventors: Alan Glyn Davies, Twickenham (GB); Steven William Shiel, Twickenham (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/713,636

(22) Filed: Nov. 14, 2003

(65) Prior Publication Data

US 2004/0131577 A1 Jul. 8, 2004

Related U.S. Application Data

(63) Continuation of application No. PCT/US02/15281, filed on May 13, 2002.

(30) Foreign Application Priority Data

May 14, 2001 (GB) .................................. 0111720.9

(51) Int. Cl.
*A61Q 5/06* (2006.01)
*A61Q 5/12* (2006.01)
(52) U.S. Cl. .................. 424/70.12; 424/70.1; 424/70.6
(58) Field of Classification Search ............... 424/70.6, 424/70.12
See application file for complete search history.

(56) References Cited

U.S. PATENT DOCUMENTS

| 4,529,586 | A | | 7/1985 | De Marco |
| 4,559,227 | A | * | 12/1985 | Chandra et al. ............ 510/122 |
| 4,563,347 | A | | 1/1986 | Starch |
| 4,597,962 | A | | 7/1986 | Grollier |
| 4,673,568 | A | | 6/1987 | Grollier |
| 4,749,656 | A | | 6/1988 | Ellerbe |
| 5,143,518 | A | | 9/1992 | Madrange |
| 5,164,522 | A | | 11/1992 | McCarthy |
| 5,439,677 | A | | 8/1995 | Villamarin |
| 5,474,835 | A | | 12/1995 | McCarthy |
| 5,616,758 | A | | 4/1997 | McCarthy |
| 5,635,163 | A | | 6/1997 | Hansenne |
| 5,807,955 | A | | 9/1998 | Berger |
| 5,856,544 | A | | 1/1999 | Czech |
| 5,958,390 | A | | 9/1999 | Sanner |
| 6,143,286 | A | * | 11/2000 | Bhambhani et al. ....... 424/70.1 |

FOREIGN PATENT DOCUMENTS

| EP | 0479000 A2 | 4/1992 |
| EP | 0275707 B1 | 5/1992 |
| WO | WO-92/00303 A1 | 1/1992 |
| WO | WO-99/32539 A1 | 7/1999 |
| WO | WO-99/49836 A1 | 10/1999 |
| WO | WO-02/47632 A2 | 6/2002 |

* cited by examiner

*Primary Examiner*—Jyothsna Venkat
(74) *Attorney, Agent, or Firm*—Brian M. Bolam; Marianne Dressman; Tara M. Rosnell

(57) ABSTRACT

The present invention relates to a hair care composition comprising a terminal aminofunctional polysiloxane, which provides improved durable conditioning particularly when utilised in conjunction with a hair colouring composition.

13 Claims, No Drawings

US 7,211,243 B2

TERMINAL AMINOFUNCTIONAL POLYSILOXANE HAIR CONDITIONING COMPOSITIONS AND THEIR USE IN HAIR COLORING COMPOSITIONS

CROSS REFERENCE TO RELATED APPLICATION

The application is a continuation of International application PCT/US02/15281 (Case CM2567) filed on May 13, 2002.

TECHNICAL FIELD OF THE INVENTION

The present invention relates to amodimethicone materials and their use in hair conditioning compositions and in particular hair colouring compositions.

BACKGROUND OF THE INVENTION

The alteration of the colour of hair by the application of hair dyes is well known.

In order to provide the consumer with the hair colour and intensity of shade desired, a very complex chemical process is utilised. The hair dyeing molecules are typically produced from the reaction of at least one oxidative colouring agent with an oxidising agent which are formed in situ on the hair of consumers and typically in an aggressive environment at ca pH 10 and in the presence of an alkalising agent. Moreover, this process is repeated regularly by the consumer in order maintain the desired hair colour and intensity of the hair colour shade and ensure continual, even coverage of the hair including coverage of new hair growth.

The manufacturer of such products is also required to work within a large number of constraints. Since these products are being placed in direct contact with the consumers' skin and potentially accidental contact with the eye or ingestion (for example) can occur during the dyeing process, the formulation must meet rigorous safety requirements and not cause any allergic reaction. In addition to meeting these requirements, the products must also be optically and olfactory pleasing to the consumer. In particular, the products need to meet certain physical parameters in order to ensure that the product can be easily applied to the hair by the consumer to provide the desired effect, without unintentional staining of the consumers clothes, skin or other objects.

The chemistry involved in the hair dyeing process may result in some damage to the hair which is permanent. Damaging effects include tangling, brittleness and dryness. Consequently there is a need to provide the hair dye composition or hair dyeing kit with a conditioning component in order to combat this damage and improve at least the consumers' perception of the condition of the hair. This is required not only immediately after the hair dyeing process has taken place and during the subsequent blow drying and styling but is an on-going consumer need during the post dyeing washing cycle until the next hair dyeing cycle.

The use of conditioning compositions is well known in the art and they are incorporated as part of conventional shampoo and conditioning regimes as well as in so called two-in-one shampoo conditioners. Their use in hair dyeing kits is also well known. Typically conditioners are provided in a sachet for use in the final rinse, after dyeing is completed. These conditioners such as amino silicones as described for example in U.S. Pat. No. 4,563,347, EP 275 707 and WO99/49836 usually provide an acceptable immediate improved feel of the hair to the consumer such as improved lubrication resulting in an improved ease of combing and detangling. However, this conditioning benefit is not durable over a number of hair washing cycles such that the consumer becomes dissatisfied with the condition of the hair during the course of the post dyeing cycle until the next dyeing treatment and/or conditioning treatment.

Unfortunately durable conditioning cannot be achieved by simply increasing the levels of conditioning material in the composition. In fact, if excessive conditioner is applied, the initial feel of the hair becomes heavy and greasy resulting in a reduction of hair volume, stickiness and a lack of hair shine. Moreover increasing the amount of conditioner also results in increased costs. These negatives are all completely unacceptable to the consumer.

Moreover, if the nature or the amount of the conditioning material is such that it is sustained on the hair during the post dyeing wash cycle such that significant amounts are still present on the hair at the start of the next colouring cycle, the performance of the dyeing process cannot be predicted and may be detrimentally effected. Such a result is equally undesirable for the consumer.

Progress has however been made in the field of hair conditioning materials and in particular compounds such as amodimethicone have been identified as delivering improved conditioning benefits. In particular amino substituted silicones wherein the amino functional group is randomly positioned along the silicone chain backbone as described in U.S. Pat. No. 4,529,586, U.S. Pat. No. 5,143,518, U.S. Pat. No. 5,439,677, U.S. Pat. No. 5,616,758, U.S. Pat. No. 5,856,544 and U.S. Pat. No. 5,856,544, have been described as providing improved conditioning properties.

Cationic silicone compounds have also been described in the art for improved bonding to cellulose and proteineous materials. For example silicone compounds having randomly positioned quaternary amino functional groups are described in U.S. Pat. No. 5,616,758 which describes cationic amino silicone compounds suitable for use in amongst others hair conditioning applications. Similarly WO92/00303, U.S. Pat. No. 5,474,835, U.S. Pat. No. 532,817, U.S. Pat. No. 5,164,522, U.S. Pat. No. 5,143,518, U.S. Pat. No. 710,314, U.S. Pat. No. 4,749,656, U.S. Pat. No. 4,673,568 and U.S. Pat. No. 4,597,962 describe hair treatment compositions comprising such cationic silicones for improved conditioning WO99/32539 describes multicationic polymers which are water miscible and suitable for formulating in products based on solvents or carriers which have high polarity such as laundry and hair care products.

However, there is still a need to provide durable conditioning materials especially for use in hair dye compositions which have the required initial deposition without any greasy feel negatives after the initial application and have retention over time and which do not negatively affect the performance of the next hair dyeing cycle.

There is also a need to provide a hair dye composition which does not necessarily require a separate post hair dyeing conditioning step wherein the conditioning component is preferably incorporated within the hair dying composition.

SUMMARY OF THE INVENTION

The present invention relates to a hair care composition comprising an amino functional polysiloxane having at least one terminal amino functional group as defined hereinafter, which provides improved conditioning particularly when utilised in combination with a hair colouring composition.

DETAILED DESCRIPTION OF THE INVENTION

As used herein the hair treated may be "living" i.e. on a living body or may be 'non-living' i.e. in a wig, hairpiece or other aggregation of non-living fibres, such as those used in textiles and fabrics. Mammalian, preferably human hair is preferred. However wool, fur and other melanin containing fibres are suitable substrates for the compositions according to the present invention.

The hair care composition according to the present invention comprises at least one or a mixture of an amino functional polysiloxane compound having at least one terminal amino functional group according to the formula:

wherein; A represents $R_2SiO$, wherein R is an alkyl group of 1 to 5 carbons, or a phenyl group, or an alkoxy group or an hydroxy group, Q, is an amine functional group of the formula $-R^2Z$, $R^2$, is a divalent alkylene radical of 3 to 6 carbons, preferably trimethylene, pentamethylene, $-CH_2CHCH_3CH_2-$, or $-CH_2CH_2CHCH_3CH_2-$, Z, is $-N(R^3)2$ or $-NR^3(CH_2)_nN(R^3)_2$, $R^3$, is individually an H atom or alkyl group of 1 to 20 carbon atoms or phenyl or benzyl, and wherein: x is from 1 to 3000, y is from 0 to 3, z is from 1 to 3, n is from 2 to 6.

Preferably, R is an alkyl group of 1 to 5 carbons, or a phenyl group more preferably a methyl group, Q, is an amine functional group of the formula $-R^2Z$, $R^2$, is a divalent alkylene radical of 3 to 6 carbons, preferably trimethylene, pentamethylene, $-CH_2CHCH_3CH_2-$, or $-CH_2CH_2CHCH_3CH_2-$, more preferably a propyl or an isopropyl group, Z, is $-N(R^3)2$ or $-NR^3(CH_2)_n N(R^3)2$, more preferably $NH_2$ or $NHCH_2CH_2NH_2$, $R^3$, is individually an H atom or alkyl group of 1 to 20 carbon atoms or phenyl or benzyl, and wherein: x, is from 1 to 3000, more preferably is from 10 to 400, even more preferably from 70 to 150 and most preferably from 90 to 120, y is from 0 to 3, more preferably from 0 to 1, z is from 1 to 3, more preferably 1 and n is from 2 to 6.

Alternatively or in addition to the above described terminal aminofunctiomal polysiloxanes, the hair care compositions comprise an aminofunctional comprising alternating units of:
(i) a polysiloxane according to the following formula:

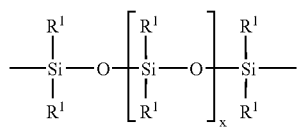

and
(ii) a divalent organic moiety comprising at least one nitrogen atom and
(iii) a monovalent organic moiety, preferably comprising at least one nitrogen atom, wherein said nitrogen atom is located at a terminal position of said polysiloxane, and wherein:
$R^1$ is an alkyl group of 1 to 5 carbons, or a phenyl group, or an alkoxy group or an hydroxy group and x is from 1 to 3000.

It has been surprisingly found that the positioning of the amino group at the terminal position of the polysiloxane chain provides the polysiloxanes with significantly improved conditioning performance initially and at least parity conditioning performance over a number of washing cycles. Terminal positioning of the amino group has been shown to significantly improve the clean feel properties of hair, whilst delivering excellent conditioning benefits such as easy detangling. Graft amino silicone polymers show significant issues of sticky and coated hair feel versus equivalent terminal amino functional polysiloxanes.

It has also been found that a number of other factors may be selected to beneficially influence the performance of the terminal aminofunctional polysiloxane, such as molecular weight, viscosity, the amine type, the linker type and the charge density.

Preferably, the viscosity of the aminofunctional polysiloxane should be selected such that it is in a range of from 10 cps to 3000 cps, preferably from 100 to 500 cps.

Whilst not being bound by theory it is believed that viscosity is proportional to polymer molecular weight and inversely proportional to the degree of branching. Viscosity will impact spreading on hair and ease of processing in the composition. Thus molecular weight also influences both of these important parameters.

The molecular weight of said aminofunctional polysiloxane is preferably from 1000 to 50000, more preferably from 1500 to 35000.

Whilst not intending to be bound by theory it is believed that increasing the charge density, to a point, provides more affinity for negatively charged, damaged hair, thus improving substantivity and durability through the colour cycle. If charge density is too high, the surfactancy of the silicone is increased to a point where wash-off is achieved too easily and durability thus reduced.

According to the present invention, the hair care composition comprises from 0.1% to 10%, preferably from 0.5% to 5%, most preferably from 1% to 3% by weight of the total composition applied to the hair of the terminal amino functional polysiloxane compound. As a result of the improved performance of the terminal aminofunctional siliones of the present invention typically less conditioning agent in required.

According to the present invention the terminal aminofunctional silicones can be prepared utilising methods well known in the silicone polymer industry.

In the case of a terminal functional polymer where the amine functionality is located at the end of the polymer chain, it is possible to know the number of dimethylsiloxane groups separating the amine groups. Moreover, it is possible to control and manipulate the number of dimethylsiloxane groups separating the amine groups, during manufacture of the polymer. Conversely, in the case of a graft functional polymer where the amine functionality can be located anywhere along the polymer chain (with the exception of the very end of the polymer, which is end-capped with trimethylsilyl groups) it is not possible to know, or to control and manipulate the number of dimethylsiloxane groups separating the amine groups.

In preparation of the amine silicone, the choice of amine modified monomer dictates the positioning of the amine functionality on the final polymer. For a terminal amine silicone, it is necessary to prepare amine modified end capping monomer (often referred to as M'). This is a monofunctional siloxy group of the formula $R_2R^1SiO_{1/2}$ where R represents independently a saturated or unsaturated monovalent hydrocarbon (especially methyl) and $R^1$ represents an amine group such as aminopropyl or aminoethylaminopropyl. The polymerisation process is well known in the art and involves the reaction by hydrosilation of a stoichiometric amount of dimethylsiloxane (often in the form of octamethylcyclotetrasiloxane or "cyclomethicone D4") and amine modified monofunctional siloxy "end-group" described. The hydrosilation step is typically carried out in the presence of a group vm precious metal catalyst such as rhodium or platinum and in the presence of dilute sulphuric acid. The resulting polymer is often abbreviated M'D$_x$M'.

Conversely, for a graft amine silicone, it is necessary to prepare amine modified, difunctional siloxy monomer, referred to as D', of the formula $RR^1SiO_{2/2}$ where R represents independently a saturated or unsaturated monovalent hydrocarbon (especially methyl) and $R^1$ represents an amine functional group such as aminopropyl or aminoethylaminopropyl. In this case, the polymerisation process via hydrosilation reaction, requires a stoichiometric amount of dimethylsiloxane (often in the form of octamethylcyclotetrasiloxane or "cyclomethicone D4") and amine modified, difunctional siloxy monomer as described and additional non-amine modified, monofunctional siloxy "end-capping" groups, referred to as M, of the formula $R_3SiO_{1/2}$ where R represents independently a saturated or unsaturated monovalent hydrocarbon (especially methyl). As stated previously, the hydrosilation step is typically carried out in the presence of a group VIII precious metal catalyst such as rhodium or platinum and in the presence of dilute sulphuric acid.

It has now been surprisingly found that the spacing (i.e. the number of dimethylsiloxane groups) between amine functional groups is important in delivering best conditioning profile and in obtaining efficient conditioning; that is to provide positive hair benefits from a silicone deposition level that is not so high as to cause negative hair attributes such as coating or unclean feel.

It has further been found that the compositions according to the present invention when utilised in conjunction with a hair colouring composition provide, not only the desired initial conditioning as determined by the Sensory Technical Test Method described hereinafter but also provide conditioning which is also maintained over a number of hair washing cycles.

Hair Colouring Agents

The composition according to the present application finds particular utility in hair colouring compositions especially oxidative hair colourants wherein the hair is subjected to a particularly aggressive environment.

Oxidative Hair Colouring Agents

A preferred hair colouring agent for use herein is an oxidative hair colouring agent. The concentration of each oxidative hair colouring agent in the colouring compositions according to the present invention is preferably from about 0.0001% to about 5% by weight. The exact amount is dependant upon the end shade required. Typically blond shades comprise from 0.0001% to 1.00%, red shades comprise 0.0010% to 4%, brown shades comprise 0.0100% to 4.00% and black shades comprise 0.100 to 4.00% by weight of the total composition on the hair.

Any oxidative hair colouring agent can be used in the compositions herein. Typically, but without intending to be limited thereby, oxidative hair colouring agents, consist essentially of at least two components, which are collectively referred to as dye forming intermediates (or precursors). Dye forming intermediates can react in the presence of a suitable oxidant to form a coloured molecule.

The dye forming intermediates used in oxidative hair colorants include: aromatic diamines, aminophenols, various heterocycles, phenols, napthols and their various derivatives. These dye forming intermediates can be broadly classified as; primary intermediates and secondary intermediates. Primary intermediates, which are also known as oxidative dye precursors, are chemical compounds which become activated upon oxidation and can then react with each other and/or with couplers to form coloured dye complexes. The secondary intermediates, also known as colour modifiers or couplers, are generally colourless molecules which can form colours in the presence of activated precursors/primary intermediates, and are used with other intermediates to generate specific colour effects or to stabilise the colour.

Primary intermediates suitable for use in the compositions and processes herein include: aromatic diamines, polyhydric phenols, amino phenols and derivatives of these aromatic compounds (e.g., N-substituted derivatives of the amines, and ethers of the phenols). Such primary intermediates are generally colourless molecules prior to oxidation.

While not wishing to be bound by any particular theory it is proposed herein that the process by which colour is generated from these primary intermediates and secondary coupler compounds generally includes a stepwise sequence whereby the primary intermediate can become activated (by oxidation), and then enjoins with a coupler to give a dimeric, conjugated coloured species, which in turn can enjoin with another 'activated' primary intermediate to produce a trimeric conjugated coloured molecule.

Oxidative Dye Precursors

In general terms, oxidative dye primary intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear coloured. For example, oxidative primary intermediates capable of forming coloured polymers include materials such as aniline, which has a single functional group and which, on oxidation, forms a series of conjugated imines and quinoid dimers, trimers, etc. ranging in colour from green to black. Compounds such as p-phenylenediamine, which has two functional groups, are capable of oxidative polymerization to yield higher molecular weight coloured materials having extended conjugated electron systems. Oxidative dyes known in the art can be used in the compositions according to the present invention. A representative list of primary intermediates and secondary couplers suitable for use herein is found in Sagarin, "Cosmetic Science and Technology", "Interscience, Special Ed. Vol. 2 pages 308 to 310. It is to be understood that the primary intermediates detailed below are only by way of example and are not intended to limit the compositions and processes herein.

The primary intermediates can be used herein alone or in combination with other primary intermediates, and one or more can be used in combination with one or more couplers. The choice of primary intermediates and couplers will be determined by the colour, shade and intensity of coloration which is desired. The primary intermediates and couplers can be used herein, singly or in combination, to provide dyes having a variety of shades ranging from ash blonde to black; these are: pyrogallol, resorcinol, p-toluenediamine, p-phenylenediamine, o-phenylenediamine, m-phenylenediamine, o-aminophenol, p-aminophenol, 4-amino-2-nitrophenol, nitro-p-phenylenediamine, N-phenyl-p-phenylenedianine, m-aminophenol, 2-amino-3-hydroxypyridine, 1-napthol, N,N bis (2-hydroxyethyl)p-phenylenediamine, 4-amino-2-hydroxytoluene, 1,5-dihydroxynapthalene, 2-methyl resorcinol and 2,4-diaminoanisole. These can be used in the molecular form or in the form of peroxide-compatible salts.

For example low intensity colours such as natural blond to light brown hair shades generally comprise from about 0.001% to about 5%, preferably from about 0.1% to about 2%, more preferably from about 0.2% to about 1% by weight of colouring composition of total oxidative dyeing agents and may be achieved by the combination of primary intermediates such as 1,4-diamino-benzene, 2,5-diamino toluene, 2,5-diamino-anisole, 4-aminophenol, 2,5-diamino-benzyl alcohol and 2-(2',5'-diamino)phenyl-ethanol with couplers such as resorcinol, 2-methyl resorcinol or 4-chloro resorcinol.

Similarly combination of the above primary intermediates with couplers, such as, 5-amino-2-methyl phenol and 1,3-diamino-benzene derivatives such as 2,4-diamino-anisole at levels of from about 0.5% to about 1% of total dyeing agents can lead to medium intensity red colours. High intensity colours such as blue to blue-violet hair shades can be produced by the combination of the above primary intermediates with couplers such as 1,3-diamino-benzene or its derivatives such as 2,5-diamino-toluene at levels of from about 1% to about 6% by weight of composition of total dyeing agents. Black hair colours can be obtained by combining the aforementioned primary intermediates with couplers such as 1,3-diaminobenzene or its derivatives.

Non-Oxidative and Other Hair Colouring Agents

The hair colouring compositions of the present invention may, in addition to or instead of an oxidative hair colouring agent, include non-oxidative and other dye materials. Optional non-oxidative and other dyes suitable for use in the hair colouring compositions and processes according to the present invention include both semi-permanent, temporary and other dyes. Non-oxidative dyes as defined herein include the so-called 'direct action dyes', metallic dyes, metal chelate dyes, fibre reactive dyes and other synthetic and natural dyes. Various types of non-oxidative dyes are detailed in: 'Chemical and Physical Behaviour of Human Hair' 3rd Ed. by Clarence Robbins (pp 250–259); 'The Chemistry and Manufacture of Cosmetics'. Volume IV. 2nd Ed. Maison G. De Navarre at chapter 45 by G. S. Kass (pp 841–920); 'cosmetics: Science and Technology' 2nd Ed., Vol. II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Oxidising Agents

The hair colouring compositions herein preferably comprise at least one oxidising agent, which may be an inorganic or organic oxidising agent. The oxidising agent is preferably present in the colouring composition at a level of from about 0.01% to about 10%, preferably from about 0.01% to about 6%, more preferably from about 1% to about 4% by weight of the composition.

Inorganic Oxidising Agents

A preferred oxidising agent for use herein is an inorganic peroxygen oxidising agent. The inorganic peroxygen oxidising agent should be safe and effective for use in the compositions herein. Preferably, the inorganic peroxygen oxidising agents suitable for use herein will be soluble in the compositions according to the present invention when in liquid form or in the form intended to be used. Preferably, inorganic peroxygen oxidising agents suitable for use herein will be water-soluble. Water soluble oxidising agents as defined herein means agents which have a solubility to the extent of about 10 g in 1000 ml of deionised water at 25° C. ("Chemistry" C. E. Mortimer. 5th Edn. p 277).

The inorganic peroxygen oxidising agents useful herein are generally inorganic peroxygen materials capable of yielding peroxide in an aqueous solution. Inorganic peroxygen oxidising agents are well known in the art and include hydrogen peroxide, inorganic alkali metal peroxides such as sodium periodate, sodium perbromate and sodium peroxide, and inorganic perhydrate salt oxidising compounds, such as the alkali metal salts of perborates, percarbonates, perphosphates, persilicates, persulphates and the like. These inorganic perhydrate salts may be incorporated as monohydrates, tetrahydrates etc. Mixtures of two or more of such inorganic peroxygen oxidising agents can be used if desired. While alkali metal bromates and iodates are suitable for use herein the bromates are preferred. Highly preferred for use in the compositions according to the present invention is hydrogen peroxide.

In preferred colouring compositions herein the inorganic peroxygen oxidising agent is present at a level of from about 0.01% to less than about 6%, preferably from about 0.01% to about 4%, more preferably from about 1% to about 4%, more preferably from about 2% to about 3% by weight of the total composition on hair.

Preformed Organic Peroxyacid

The compositions herein may instead or in addition to the inorganic peroxygen oxidising agent(s), comprise one or more preformed organic peroxyacid oxidising agents.

Suitable organic peroxyacid oxidising agents for use in the colouring compositions according to the present invention have the general formula:

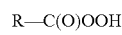

wherein R is selected from saturated or unsaturated, substituted or unsubstituted, straight or branched chain, alkyl, aryl or alkaryl groups with from 1 to 14 carbon atoms.

Conditioning Agent

The hair care composition according to the present invention preferably comprises at least one hair conditioning agent in addition to the terminal aminofunctional polysiloxane. The conditioning means agent herein can be any conditioning agent suitable for use in conditioning hair. The incorporation of an additional conditioning agent can further improve the condition of the hair.

The conditioning agent is preferably present at a level of from about 0.1% to about 25%, preferably from about 1% to about 20%, more preferably from about 5% to about 20% and especially from about 5% to about 15%, by weight of the composition.

Suitable conditioning agents for use herein include, but are not limited to, cationic surfactants, cationic polymers, insoluble silicones, non-volatile hydrocarbons, saturated C14–C22 straight chain fatty alcohols, non-volatile hydrocarbon esters, and mixtures thereof. Other suitable conditioning agents are disclosed in WO95/20939 and WO96/32919 which are incorporated herein by reference.

Preferred conditioning agents for use herein include cationic surfactants, cationic polymers, insoluble silicone conditioning agents and saturated C14–C22 straight chain fatty alcohols and mixtures thereof. Especially preferred for use herein is a mixture of cationic polymer, non-volatile silicone and C14–C22 straight chain fatty alcohols.

When present, the insoluble silicone conditioning agents are present at a level of from about 0.1 to 10%, preferably from about 0.1% to about 5%, more preferably from about 1% to about 3% by weight of composition. Suitable insoluble silicones include polyalkyl siloxanes, polyaryl siloxanes, polyalkylaryl siloxanes, polether siloxane copolymers, and mixtures thereof. The silicone conditioning agent will preferably be non-volatile. As used herein the term "non-volatile" shall mean that the material has a boiling point of at least about 260° C., preferably at least about 275° C., more preferably at least about 300° C. Such materials exhibit very low or no significant vapour pressure at ambient conditions. The term "silicone fluid" shall mean flowable silicone materials having a viscosity of less than 1,000,000 centistokes at 25° C. The term "silicone gum" shall mean flowable silicone materials having a viscosity of 1,000,000 centistokes at 25° C. or greater. The viscosity can be measured by a glass capillary viscometer as in Dow Corning, Corporate Test Method CTM0004, Jul. 20, 1920, or equivalent.

A preferred silicone material for use herein is a polydimethyl siloxane. These silicones are available for example from the General Electric Company in their Viscasil and SF96 series, and from Dow Corning in their Dow Corning 200 series.

Other suitable insoluble silicones for use herein are disclosed in WO96/32919 which is incorporated herein by reference.

When present, the cationic polymers are present at a level of from about 0.1 to 10%, preferably from about 0.1% to about 5%, more preferably from about 1% to about 3% by weight of composition. Suitable cationic polymers for use herein are disclosed in WO96/32919 which is incorporated herein by reference.

When present, the fatty alcohols are present at a level of from about 0.1% to about 20%, preferably from about 1% to about 15% and more preferably from about 3% to about 10% by weight of composition. Preferred fatty alcohols for use herein are cetyl alcohol and stearyl alcohol and mixtures thereof.

The colouring compositions used in the methods of the present invention can be formulated over a wide pH range, e.g. from about 2 to about 13, but the compositions are formulated at high pH, preferably in a pH range of from about 8 to about 12, more preferably from about 9 to about 11, most preferably from about 9.5 to 10.5.

The compositions may contain one or more optional buffering agents and/or hair swelling agents (HSAs). Several different pH modifiers can be used to adjust the pH of the final composition or any constituent part thereof. However, preferred compositions herein are substantially free of additional buffering agents, and hair swelling agents, i.e. they comprise less than about 1%, preferably less than about 0.5%, more preferably less than about 0.1% by weight of such agents.

The hair colour compositions herein, may, as will be described later herein, comprise a final composition containing a hair colouring agent and a conditioning agent which have been admixed prior to application to the hair or may comprise a single component system. As such, the compositions herein may comprise colouring kits of a number of separate components.

In oxidative colouring kits comprising a portion of inorganic peroxygen oxidising agent, such as hydrogen peroxide, which may be present in either solid or liquid form, a buffering agent solution can be used to stabilise hydrogen peroxide. Since hydrogen peroxide is stable in the pH range from 2 to 4, it is preferable to use a buffering agent having a pH within this range. Dilute acids are suitable hydrogen peroxide buffering agents.

Surfactant Materials

The compositions herein can additionally contain a surfactant system. Suitable surfactants for inclusion in the compositions for use in the invention generally have a lipophilic chain length of from about 8 to about 22 carbon atoms and can be selected from anionic, cationic, nonionic, amphoteric, zwitterionic surfactants and mixtures thereof. Particularly preferred are cationic, nonionic and mixtures thereof. Suitable surfactants for use herein are disclosed in WO98/27945 which is incorporated herein by reference in its entirety. Particularly preferred surfactants are surfactants of the general formula

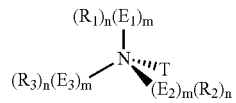

Wherein $R_1$, $R_2$, and $R_3$ represent either hydrogen or organic radicals with n equal to 0 or an integer. The radicals may be saturated, unsaturated or aromatic in nature with carbon chain lengths of 1 to 24. $R_1$, $R_2$ and $R_3$ may contain heteroatoms such as, but not limited to, oxygen, nitrogen and sulphur. $E_1$, $E_2$ and $E_3$ represent polyethyleneoxide moieties with ethyleneoxide sub-units such that m can be zero or an integer. The degree of ethoxylation of $E_1$, $E_2$ and $E_3$ can be the same or different. T represents a hydrogen that, depending on the pH and solvents used in the system, may or may not be attached to the nitrogen.

For preferred methods herein, it is preferable that the hair conditioning and colour composition comprises less than about 20% surfactant, preferably less than about 10% surfactant. It is also preferable that the hair colour altering compositions comprise less than about 5% anionic surfactant.

Optional Materials

The compositions of the present invention typically further comprise a number of other components commonly utilised in hair care compositions such as shampoos, conditioners, styling aids and colourants which are well known to those skilled in the art such as for example thickeners and diluents. Additionally a number of optional materials can be added to the compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol, benzoic acid, sodium benzoate and 2-phenoxyethanol; antioxidants such as sodium sulphite, hydroquinone, sodium bisulphite, sodium metabisulphite and thyoglycolic acid, sodium dithionite, erythrobic acid and other mercaptans; dye removers such as oxalic acid, sulphated castor oil, salicylic acid and sodium thiosulphate; $H_2O_2$ stabilisers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and p-hydroxybenzoates; moisturising agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663 as well as methyl cellulose, starch, higher fatty alcohols, paraffin oils, fatty acids and the like; solvents; anti-bacterial agents such as Oxeco (phenoxy isopropanol); low temperature phase modifiers such as ammonium ion sources (e.g. $NH_4Cl$); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; enzyme stabilisers such as water soluble sources of calcium or borate species; $TiO_2$ and $TiO_2$-coated mica; perfumes and perfume solubilizers; and zeolites such as Valfour BV400 and derivatives thereof and metal ion sequestrants such as polycarboxylates, amino polycarboxylates, polyphosphonates, amino polyphosphonates etc. and water softening agents such as sodium citrate, inorganic peroxygen oxidsing agents and enzymes.

Method of Use

It is important that hair conditioning and colouring compositions be in a form which is easy and convenient to prepare and use by the consumer, since the oxidising agent must remain in contact with the hair for a certain period of time and not run or drip off of the hair, possibly causing eye or skin irritation. In order to provide a composition, which is easy for the consumer to apply to the hair without dripping the viscosity of the composition, should be controlled.

The conditioning and colouring composition may be provided as a single composition containing all the necessary conditioning and colouring ingredients. When the colouring composition comprises oxidative colouring agents and oxidising agents, it is preferably provided in the form of two components, one of which contains the oxidative colouring agent and the second of which contains the oxidising agent. The conditioning agent may be present in either of these components or as a separate third component. When the composition is provided in the form of two components these may be made up into the composition before application to the hair or applied separately to form a single composition on the hair. Percentages and amounts when discussed in this specification refer to percentages and amounts in the final composition on the hair.

Consequently the colouring and conditioning composition can be provided as a single pack or in kit form as separately packaged components to maintain stability, and, if so desired, mixed by the user immediately prior to application to the hair.

Preferably the colouring and conditioning composition is provided in the form of at least two components, a first component comprising an oxidising agent and a second component comprising a hair colouring agent. The aminofunctional polysiloxane conditioning agent may be comprised within the first or second component or may be comprised within a third component. The first and second components can either be mixed by the user immediately prior to application to the hair or can be applied separately. In one embodiment of the present invention the oxidising component comprises a stabilised cream comprising an inorganic peroxygen oxidising agent, most generally hydrogen peroxide in an amount such that the final concentration of the colouring composition as used on the hair is from about 0.05% to about 6% by weight. It may also contain additional agents as herein before described.

The first and second components and the third component if present, are separately packaged and the separate packages may be connected (e.g. as two or three chambers in a single aerosol dispenser) or may be entirely separate (e.g. two or three non-connected sachets). Preferably, they are in the form of separately packaged but associated (e.g. in attached packages) components.

When the components are packaged separately in associated packages these may be in the form of a single package having several chambers, one chamber for each separate component. A preferred pack herein is a pack having two chambers, one chamber comprising a first component comprising a hair colouring agent and a second chamber comprising a second component comprising an oxidising agent. Either or both of the first and second components may contain a terminal aminofunctional polysiloxane, or alternatively the terminal aminofunctional polysiloxane may be present in a third chamber. The two components can be mixed either outside the pack, for example, by hand, or within the pack, for example by a mechanical means of mixing. It is preferable that the two components are mixed sufficiently in order to provide a homogeneous hair colouring composition for application to the hair. Such a pack provides a product, which is easy and convenient to use. The colouring compositions can also be packaged within blister packs and sachets. For instance, a single sachet may contain sufficient for a single application when two different sachets are mixed together. A blister pack may contain a predetermined number of the two different component compositions, each blister containing sufficient composition for one application when the two are mixed.

According to the present invention it is particularly preferred that the composition contains an oxidative colouring agent and thus according to a another aspect of the invention there is provided a method for colouring and conditioning hair comprising the steps of applying to the hair a hair colouring composition which preferably contains at least one oxidative colouring agent and at least one oxidising agent and a hair conditioning composition comprising a terminal aminofunctional polysiloxane and subsequently rinsing the composition from the hair. The terminal aminofunctional polysiloxane conditioner may be applied to the hair prior to the application of the hair colouring composition, at the same time as the hair colouring composition is applied or after the hair colouring composition has been applied.

Another aspect of the invention provides a kit for use in colouring and conditioning hair. This kit comprises (a) a hair colouring composition which contains at least one colouring agent and (b) a hair conditioning composition which comprises a terminal aminofunctional polysiloxane and (c) instructions to apply the colour composition to the hair and to leave the colouring composition on the hair and then rinse the colouring composition from the hair and to apply the hair conditioning composition to the hair in a separate step.

According to another aspect of the invention a kit is provided for use in colouring and conditioning hair comprising (a) a hair colouring composition which contains at least one colouring agent and at least one oxidising agent and (b) a separately packaged hair conditioning composition which contains a terminal aminofunctional polysiloxane conditioner. The compositions and the instructions may have any of the preferred features discussed above in the context of the method of the invention where appropriate.

The kit of the invention may comprise a series of separately packaged doses of each composition, each dose being appropriate for a single application, and the kit as a whole being sufficient to allow the consumer to carry out the method for a period.

Test Methods and Example Compositions

Treatment of Switches With Hair Care Compositions

Hair Switches

The hair switches utilised in the following test are:
Virgin light brown hair 4 g x 8" Hair, (10 switches are required per test).

Water Settings

The water settings utilised for the following tests are:
Tap water, hardness 15–16 gpg.
Water flow rate 6±0.5 L/min.
Water Temperature 37±2° C.

Sample Preparation

In order to assess the performance of the present invention on hair, which is regularly coloured, the hair switch samples utilised in the test are firstly treated with a market product hair colourant (namely L'Oreal, Excellence No. 3) according to the manufacturers' instructions. The "in-box" conditioner supplied with the colourant is not used. Following this treatment the samples are then washed as described below.
1. Wet switch for 10 seconds.
2. Apply 0.4 ml of Prell shampoo on the hair switch, using a syringe.
3. Lather for 30 seconds using milking action, distributing shampoo on both sides of hair switch.
4. Rinse for 30 seconds.
5. Steps 2–4 are repeated 4 times.
6. Hot air dry, brushing with a vent brush, whilst blow drying on a high heat/high speed for a total of 3 minutes (1 minute on each side and 1 minute with brushing).

Initial Treatment of Sample

The switch is hung above a sink. 6.0 grams of the colouring composition to be tested is applied on the top end of the switch and spread evenly down to the bottom end, then milked into the switch. The switch is then hung in an incubator at 30° C. for 30 minutes. The switch is then rinsed with water for 2 minutes (1 minute on each side). Excess water is squeezed out of the switch. The initial average sensory clean index values and average sensory wet conditioning index values are calculated by carrying out the sensory test described herein on the wet switches.

Final Treatment of Sample

The switches are then washed as described 18 times.
1. Wet switch for 10 seconds.
2. Apply 0.4 ml of Pantene 2 in 1 shampoo on the hair switch, using a syringe.
3. Lather for 30 seconds using milking action, distributing shampoo on both sides of hair switch.
4. Rinse for 30 seconds.
5. Repeat steps 2, 3 and 4 once.
6. Hot air dry, brushing with a vent brush, whilst blow drying on a high heat/high speed for a total of 3 minutes (1 minute on each side and 1 minute with brushing).
7. The final average sensory clean and wet conditioning index values are calculated by carrying out the sensory tests as described herein from the sample wetted again for 10 seconds.

Sensory Evaluation and Descriptive Analysis Panels

Sensory evaluation is designed to measure, analyse and interpret reactions to product characteristics as perceived by the senses of sight, smell, taste, touch and hearing. A commonly used sensory evaluation technique is descriptive analysis. Descriptive analysis is a complete, detailed and objective characterization of the sensory properties of a product using screened and qualified panellists that are specifically trained for this purpose. Descriptive analysis provides information about the perceived sensory properties (or attributes) and the strength of each sensory attribute in quantitative terms. Panellists are trained to rate the intensity of a large number of sensory properties, while ignoring personal preferences. Each sensory attribute is meticulously defined, and panellists are presented with reference materials that represent high, medium and low intensities of each sensory attribute. Panellists work in isolation in a sensory booth, and assess all sensory characteristics of one sample before moving to the next sample. Care is taken to blind and randomise the samples, and to control the environment (lighting, temperature, humidity).

A descriptive analysis panel requires 10 panellists, because the high level of training ensures a low level of variability in the data (small standard deviations). Panellists only qualify when their ratings are consistent from test-to-test, when their ratings are consistent with that of the panel, and when they are sensitive enough to discriminate small differences. Performance of descriptive analysis panels and individual panellists is monitored closely. Typically, each product is evaluated by all panellists once or twice, and the mean attribute ratings across the panellists or panellist means is calculated. Because the intensity scores are recorded in relation to a universal scale, the relative intensities among attributes and among products can be compared. Descriptive analysis ratings are used for quality control and shelf life studies, for product development, and for claim substantiation. The ASTM Guideline E 1958-98 "Standard Guide for Sensory claim Substantiation" states that descriptive analysis data are suitable for claim substantiation if the panel shows good consistency and robustness, and when the relationship between descriptive sensory attributes and consumer responses is established.

Descriptive Analysis Panel

A panel consisting of 10 trained females, was used to conduct the tests.

No Residue

Technique: After the switch is combed, assess the amount of coating on the dry hair sample using a 'milking' motion with thumb and index/middle finger. Assess the amount of coating you can feel on the hair when milking.
Definition: No Residue=The lack of product coating or residue felt on the hair sample (regardless of the type of coating), from not coated=0 (low anchor) to very coated=100(high anchor).

Not Sticky

Technique: After the switch has been combed, assess the sticky feel by pressing the thumb and index finger to the switch using a quick and light motion and assess the amount of adhesion felt between the fingers and switch when releasing.
Definition: Sticky=The degree to which the residue on hair seems sticky in nature (as opposed to waxy, oily, stiff etc.). This attribute is specific in quantifying the amount of a specific type of coating. The scale is from not sticky=0 (high anchor) to very sticky=100 (low anchor).

Ease of Detangling:

Technique: With the wide end of the comb, comb 3 times to remove tangles. Assess the difficulty of removing tangles from the sample hair. If longer is needed to remove all the tangles, continue to comb with wide end until all tangles are removed.

Definition: Hard to detangle=The time and force required remove all tangles from the sample hair with the wide end of a comb, from very easy (one stroke)=0 to very difficult=100 (many strokes/lot of force required).

Not Coarse:

Technique: After the hair has been combed through, assess the coarse or rough feel of the hair by rubbing across the switch with thumb, index and middle fingers in a horizontal direction.

Definition: Not Coarse=The absence of coarse or rough feel on the hair, from no apparent roughness=0 to very rough=100.

Resistance to Milking

Technique: After the switch has been combed, assess the resistance encountered when moving the fingers down the length of the switch using a milking motion (1 stroke/second).

Definition: Resistance to Milking=the degree of resistance encountered, from very resistant (not slippery)=100, to not resistant (very slippery)=0.

Shine

Technique: Assess the shine of the hair when the switch is bent at a sharp angle under a consistent direct light source.

Definition: The visual amount of shine observed under the above conditions, from not shiny (dull)=0 to very shiny=100.

Deposition of Amino Silicone by X-Ray Fluorescence Spectroscopy

X-Ray Fluorescence (XRF) spectroscopy is used to measure the level of amino functional silicone on the hair switch (reported as parts per million (ppm) Si on hair). Hair switches are prepared as described above.

Example COMPOSITIONS

The colouring composition was made up before each application by mixing the peroxide cream with the dye cream, and where applicable, the amino functional silicone to be tested. The dye cream and the peroxide cream compositions are prepared as described herein after. The amino functional silicone is mixed with the peroxide cream until a dispersion, with an average particle size of between 10 and 20 microns is made. The peroxide cream with amino functional silicone is then mixed with the dye cream.

Examples of Final Dye Cream Formulations

The following dye cream formulations are to be mixed 1:1:0.02 with the peroxide cream and the amino functional silicone.

| Dye Cream Formula for Blondes | % in use |
|---|---|
| Water | QS to 100 |
| Emulsion Base | 22.5000 |
| Dye premix | 14.0000 |
| 30% Aqueous Ammonium hydroxide | 6.0000 |

Examples of Dye Emulsion Base Formulations

The following are examples of the emulsion base premix formulation:

| | % w/w in Use |
|---|---|
| Dye Emulsion Base Formula A | |
| Water | As Required |
| Ceteareth 25 | 0.5400 |
| Cetyl Alcohol | 0.8100 |
| Stearyl Alcohol | 1.6300 |
| Sodium Benzoate | 0.0557 |
| Phenoxyethanol | 0.0668 |
| Benzyl Alcohol | 0.0668 |
| Steareth 2 | 0.2700 |
| Tetrasodium EDTA | 0.0223 |
| Di-PEG-2 Soyamine IPDI | 0.2115 |
| Lowenol S216 from Lowenstein | 2.1150 |
| Dye Emulsion Base Formula B | |
| Water | As Required |
| Ceteareth 25 | 1.5000 |
| Cetyl Alcohol | 2.2500 |
| Stearyl Alcohol | 2.2500 |
| Sodium Benzoate | 0.0557 |
| Phenoxyethanol | 0.0668 |
| Benzyl Alcohol | 0.0668 |
| Tetrasodium EDTA | 0.0223 |
| Dye Emulsion Base Formula C | |
| Water | As Required |
| Ceteareth 25 | 1.5000 |
| Cetyl Alcohol | 2.2500 |
| Stearyl Alcohol | 2.2500 |
| Sodium Benzoate | 0.0557 |
| Phenoxyethanol | 0.0668 |
| Benzyl Alcohol | 0.0668 |
| Tetrasodium EDTA | 0.0223 |

Dye Cream Emulsion Making Methods

The Dye Base Emulsions described and exemplified hereinabove can be manufactured utilising any one of the standard approaches, these include:

Oil in water process

Phase Inversion process

One-pot process

An example Dye Base Emulsion making method is given below.

One-Pot Process for Making Dye Cream Emulsion

1. Add water to vessel. Heat to above the melt temperature of the fatty alcohols with agitation.
2. Add Fatty Alcohols and any Ethoxylated Fatty Alcohols, e.g. Ceteareth-25, Cetyl, Stearyl and Steareth-2, and allow to melt. Increase agitation.
3. If used add other surfactants such as Dihydroxyethyl Soyamine Dioleate (Lowenol S216 from Lowenstein) and/or Peg-3 Cocamine (Lowenol C243 from Lowenstein) and/or PEG-5 Cocamine (Ethomeen C/15 from Akzo Nobel) and/or Di PEG-2 Soyamine IPDI.
4. Continue mixing with shear.
5. Begin cooling with shear adding preservatives at appropriate temperature.
6. Cool to room temperature, stopping shear as fatty alcohols solidify and structure builds.

Final Dye Cream Making Method

Below is an example of how the final dye cream can be manufactured:

To the dye cream emulsion add the following:
Decyl glucoside (if used) then mix to give a homogenous product
Dye premix containing: water, anti-oxidants, solvents, precursors and couplers, then mix to give a homogenous product
Ammonium hydroxide, then mix to give a homogenous final product
Dye Premix Formulations:
The following is a list of typical couplers and precursors used to formulate various shade ranges.

| |
| --- |
| p-Phenylenediamine |
| p-Aminophenol |
| N4,N4-bis Hydroxyethyl-p-PD sulphate |
| o-Aminophenol |
| p-Methylaminophenol |
| 2,5,Diamonotoluene Sulphate |
| m-Aminophenol |
| 4-amino-2-hydroxytoluene |
| Resorcinol |
| 2-methyl resorcinol |
| 2-Amino-3-Hydroxypyridine |
| 2-Amino-4-Hydroxyethylaminoanisole sulphate |
| 2-methyl-5-hydroxyethylaminophenol |
| m-Phenylenediamine.sulphate |
| 1-phenyle-3-methyl-5-pyrazolone |
| Naphthol |
| 1-Hydroxy-4-Aminobenzene |

Additionally the dye premix formulations may comprise the following additional materials:—

| |
| --- |
| Water |
| Reducing Agents such as Sodium Sulphite |
| Anti-oxidants such as D and L-Ascorbic Acid |
| Metal Chelants such as EDTA |
| Solvents such as glycols and alchols |

Examples of Total Dye Levels Used in Various Shades

| Shade | % w/w in use |
| --- | --- |
| Blondes | 0.0001 to 4.0000 |
| Reds | 0.0010 to 4.0000 |
| Browns | 0.0100 to 4.0000 |
| Blacks | 0.1000 to 4.0000 |

Dye Premix Making Method
The dye premix may be manufactured using any one of the standard approaches such as
oil in water process
phase inversion process
one pot process An example of a dye premix manufacturing method is as follows:
1. With mixing add water to the following: solvents, anti-oxidants, precursors and couplers
2. If required warm to solubilize
3. Cool to room temperature Hydrogen Peroxide Cream Making Method Example of a Hydrogen Peroxide Emulsion Base

| Hydrogen Peroxide Emulsion Base Formula | % w/w in Formula |
| --- | --- |
| Purified Water | QS to 100 |
| Ceteareth-25 | 4.17 |
| Cetyl Alcohol | 6.25 |
| Stearyl Alcohol | 6.25 |

Hydrogen Peroxide Emulsion Base Method
The Hydrogen Peroxide Emulsion Base described herein can be made by any of the standard approaches, these include:
Oil in water process
Phase Inversion process
One-pot process An example of a Hydrogen Peroxide Emulsion Base making method is given below.

One-Pot Process for Making Hydrogen Peroxide Emulsion Base
1. Add water to vessel. With agitation heat to above the melt temperature of the fatty alcohols
2. Add Fatty Alcohols and any Ethoxylated Fatty Alcohols and allow to melt. Increase agitation.
3. Continue mixing with shear until emulsion has formed
4. Begin cooling stopping shear at appropriate temperature.
5. Cool to room temperature Chelator Premix to Stabilise Peroxide

| | % w/w in Formula |
| --- | --- |
| Purified Water | QS to 15.0000 |
| Metal Chelators | 0.0010 to 1.0000% |
| Phosphoric Acid and/or Sodium Hydroxide | Adjust to pH 1–5 |

Example Making Method for Chelant Premix
1. Dissolve the chelants in the water phase
2. Adjust pH with phosphoric acid and/or sodium hydroxide as required 6% Hydrogen Peroxide Cream

| | % w/w Addition |
| --- | --- |
| Hydrogen Peroxide Emulsion Base | 36.00 |
| Chelator Premix | 15.00 |
| Water | QS to 100 |
| 35% Hydrogen Peroxide | 17.71 |
| pH Adjustment Gap | To pH 1–5 |

Example Making Method for 6% Hydrogen Peroxide Cream
To the Hydrogen Peroxide Emulsion Base add the following with agitation: Water, Chelant Premix and 35% Hydrogen Peroxide Solution, mix until homogeneous. Adjust pH to between one and five with appropriate amounts of phosphoric acid and/or sodium hydroxide 9% Hydrogen Peroxide Cream

|  | % w/w Addition |
| --- | --- |
| Hydrogen Peroxide Emulsion Base | 36.00 |
| Chelator Premix | 15.00 |
| Water | QS to 100 |
| 35% Hydrogen Peroxide | 26.57 |
| pH Adjustment Gap | To pH 1–5 |

Example Making Method for 9% Hydrogen Peroxide Cream

To the Hydrogen Peroxide Emulsion Base add the following with agitation: Water, Chelant Premix and 35% Hydrogen Peroxide Solution, mix until homogeneous. Adjust pH to between one and five with appropriate amounts of phosphoric acid and/or sodium hydroxide Results:

Example 1 is a hair dye composition according to the present invention described herein above which is a blond shade comprising 9% hydrogen peroxide and 2% terminal amino functional silicone of the structure M'D102M' where M' represents aminopropyldimethylsilyl and D represents dimethylsiloxane.

Reference 1 is a hair dye composition which comprises the same dye cream formula and hydrogen peroxide cream formulation as used in example 1, and 2% of a commercially available graft amino functional silicone (Q2-8220 supplied by the Dow Corning Company).

Further example formulations where made. These were identical to Example 1 but with the following terminal amino functional silicones added in place of the terminal amino silicone described in example 1:

| Example No | M'D$_x$M' Value of x | M' |
| --- | --- | --- |
| Example 2 | 14 | aminopropyldimethylsilyl |
| Example 3 | 43 | aminopropyldimethylsilyl |
| Example 4 | 102 | aminopropyldimethylsilyl |
| Example 5 | 165 | aminopropyldimethylsilyl |
| Example 6 | 220 | aminopropyldimethylsilyl |

D = dimethylsiloxane.

|  | Initial | | Long-Term | |
| --- | --- | --- | --- | --- |
|  | E.g. 1 | Ref. 1 | E.g. 1 | Ref. 1 |
| Dry Hair Assessment Conditioning Attributes | | | | |
| Dry Not Coarse | 74 |  | 75 | 81 | 81 |
| Dry Ease of Detangling | 91 |  | 89 | 94 | 95 |
| Dry Resistance to Milking | 81 | s | 72 | 18 | 18 |
| Clean Feel Attributes | | | | |
| Dry Shine | 75 | s | 68 | 74 | s | 67 |
| Dry No Residue | 80 | s | 75 | 82 | 83 |
| Wet Hair Assessment Conditioning Attributes | | | | |
| Wet Not Coarse | 74 |  | 72 | 71 | 75 |
| Wet Ease of Detangling | 85 | s | 82 | 83 | 85 |
| Wetted Resistance to Milking | 72 | s | 66 | 71 | 73 |

-continued

|  | Initial | | Long-Term | |
| --- | --- | --- | --- | --- |
|  | E.g. 1 | Ref. 1 | E.g. 1 | Ref. 1 |
| Clean Feel Attributes | | | | |
| Wet Not Sticky | 73 | s | 56 | 73 | 71 | s denotes significant difference @ 90% using LSD method

The above sensory results demonstrate the significant improvement in conditioning profile for the terminal amino functional silicone, versus its graft analogue. The benefit is most significant on initial application of the dye where the terminal amino functional silicone does not impart a sticky feel or a feeling of high residue. Important conditioning benefits such as ease of detangling and not coarse are delivered both initially and long term.

| Wet Not Coarse/Deposition Index | | |
| --- | --- | --- |
|  | Initial | Long-Term |
| Example 2 | 0.02 | 0.16 |
| Example 3 | 0.04 | 2.30 |
| Example 4 | 0.33 | 3.49 |
| Example 5 | 0.30 | 1.16 |
| Example 6 | 0.25 | — |

The conditioning performance/weight deposited index demonstrates the more efficient conditioning achieved by the most preferred range of terminal amino functional silicones. A key consumer concern is coarse wet hair feel when washing. Alleviating this coarse feel without needing to deposit a large amount of silicone delivers most efficient conditioning, achieved with the Example 4 terminal amino silicone.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A hair care composition comprising one or more surfactants and a terminal aminofunctional polysiloxane according to the formula:

$R_{3-y}Q_y SiO[A]_x SiQ_z R_{3-z}$ wherein; A represents $R_2SiO$, wherein:

R is an alkyl group of 1 to 5 carbons, or a phenyl group, or an alkoxy group or an hydroxy group;

Q is an amine functional group of the formula —$R^2Z$;

$R^2$ is a divalent alkylene radical of 3 to 6 carbons;

Z is —$N(R^3)_2$ or —$NR^3(CH_2)_n N(R^3)_2$, $R^3$ is individually an H atom or alkyl group of 1 to 20 carbon atoms or phenyl or phenyl or benzyl;

and wherein:

X is from 70 to 150;

y is from 1 to 3;

Z is from 1 to 3; and n is from 2 to 6.

2. A hair care composition according to claim 1, wherein: R is an alkyl group of 1 to 5 carbons, or a phenyl group.

3. A hair care composition according to claim 2, wherein:

R isamethyl;

$R^2$ is —$CH_2CH_2CH_2$— or —$CH_2CHCH_3CH_2$—

Z is $NH_2$ or $NHCH_2CH_2NH_2$ and wherein x is from 90 to 120, y is 1, and z is 1.

4. A hair care composition according to claim 1, wherein said hair care composition comprises from about 0.1% to about 10% of said terminal aminofunctionalpolysiloxane by weight of the total composition applied to the hair.

5. A hair care composition according to claim 1, wherein said hair care composition further comprises at least one oxidative dye.

6. A hair care composition according to claim 1, wherein said hair care composition has a pH of form about 9 to about 11.

7. A hair care composition according to claim 1, wherein said hair care composition further comprises at least one additional conditioning agent.

8. A hair colouring and conditioning kit comprising at least two components, a first component comprising an oxidising agent and a second component comprising a hair colouring agent, wherein said kit further comprises a hair care composition according to claim 1 and wherein said hair care composition is comprised within said first component, said second component is comprised within a third component, wherein said first and said second components are mixed together immediately prior to application to the hair.

9. A packaged hair colouring and conditioning Product comprising at least two chambers, a first chamber comprising a first composition comprising an oxidising agent, and a second chamber comprising a second composition comprising an oxidative hair colouring agent, wherein said package further comprises a hair care composition according to claim 1 wherein said hair care composition is comprised within said first composition, or said second composition.

10. A packaged hair colouring and conditioning product comprising at least three chambers, a first chamber comprising a first composition comprising an oxidising agent, a second chamber comprising a second composition comprising an oxidative hair colouring agent, and a third chamber comprising a hair care composition according to claim 1.

11. A method of colouring and conditioning human or animal hair, said method comprising the steps of:
    (1) applying to the hair a hair colouring composition;
    (2) applying to the hair a hair care composition according to claim 1; and
    (3) rinsing the hair.

12. A method of colouring and conditioning human or animal hair according to claim 11, said method comprising the steps of:
    (1) applying a hair care composition according to claim 1 to the hair and optionally subsequently rinsing said composition from the hair; and then
    (2) applying a hair colouring composition to the hair and subsequently rinsing said composition from the hair.

13. A method of colouring and conditioning human or animal hair according to claim 11, said method comprising the steps of:
    (1) first applying a hair colouring composition to the hair and subsequently rinsing said composition from the hair; and then
    (2) second applying a hair care composition according to claim 1 to the hair and subsequently rinsing said composition from the hair.

* * * * *